US012366619B2

(12) United States Patent
Jin et al.

(10) Patent No.: US 12,366,619 B2
(45) Date of Patent: Jul. 22, 2025

(54) MAGNETIC RESONANCE SCANNING METHOD AND SYSTEM AND COMPUTER-READABLE STORAGE MEDIUM

(71) Applicant: GE Precision Healthcare LLC, Wauwatosa, WI (US)

(72) Inventors: Liyuan Jin, Beijing (CN); Yaan Ge, Beijing (CN); Qilin Lu, Beijing (CN); Qingyu Dai, Beijing (CN); Kun Wang, Beijing (CN)

(73) Assignee: GE Precision Healthcare LLC, Wauwatosa, WI (US)

(*) Notice: Subject to any disclaimer, the term of this patent is extended or adjusted under 35 U.S.C. 154(b) by 815 days.

(21) Appl. No.: 17/202,180

(22) Filed: Mar. 15, 2021

(65) Prior Publication Data

US 2021/0298628 A1    Sep. 30, 2021

(30) Foreign Application Priority Data

Mar. 31, 2020   (CN) .......................... 202010242820.7

(51) Int. Cl.
| *G01R 33/385* | (2006.01) |
| *G01R 33/24* | (2006.01) |
| *G01R 33/3875* | (2006.01) |
| *G01R 33/44* | (2006.01) |
| *G01R 33/54* | (2006.01) |

(52) U.S. Cl.
CPC ......... *G01R 33/385* (2013.01); *G01R 33/243* (2013.01); *G01R 33/3875* (2013.01); *G01R 33/443* (2013.01); *G01R 33/445* (2013.01); *G01R 33/543* (2013.01)

(58) Field of Classification Search
CPC .............. G01R 33/385; G01R 33/3875; G01R 33/443; G01R 33/445; G01R 33/543; G01R 33/243; G01R 33/32; G01R 33/48; A61B 5/055; A61B 5/7246
See application file for complete search history.

(56) References Cited

U.S. PATENT DOCUMENTS

| 6,466,016 B1 | 10/2002 | Miyoshi | |
| 2010/0244823 A1* | 9/2010 | Abe ................. | G01R 33/56563 324/309 |
| 2015/0362578 A1* | 12/2015 | Biber ................ | G01R 33/3875 324/309 |

(Continued)

FOREIGN PATENT DOCUMENTS

| CN | 1920592 B | 6/2011 |
| CN | 104490393 B | 4/2017 |

OTHER PUBLICATIONS

Jin, Liyuan, et al. "A Quantitative Analysis on Patient-induced B0 Field Inhomogeneity at 1.5 T MRI System." Aug. 2020. (Year: 2020).*

(Continued)

*Primary Examiner* — Rishi R Patel
(74) *Attorney, Agent, or Firm* — Fletcher Yoder, P.C.

(57) ABSTRACT

Embodiments of the present invention provide a magnetic resonance scanning method and system and a computer-readable storage medium. The method comprises: when an imaging volume of an object is at a current position, performing a current imaging scan on the imaging volume based on a predicted overall B0 field map at the current position.

20 Claims, 12 Drawing Sheets

(56) References Cited

U.S. PATENT DOCUMENTS

| | | | |
|---|---|---|---|
| 2016/0209484 A1* | 7/2016 | Bauer | G01R 33/583 |
| 2017/0192075 A1* | 7/2017 | Nakai | G01R 33/4828 |
| 2019/0064302 A1* | 2/2019 | Feiweier | G01R 33/56563 |
| 2020/0003856 A1* | 1/2020 | Constable | G01R 33/3808 |

OTHER PUBLICATIONS

Jezzard et al., "Correction for Geometric Distortion in Echo Planar Images from B0 Filed Variations," Magnetic Resonance in Medicine, Jun. 30, 1995, 34(1):65-73, 9 pages.

CN application 202010242820.7 filed Mar. 31, 2020—Office Action issued Apr. 27, 2024; 12 pages.

CN104490393 Abstract—English Translation; Espacenet Jul. 25, 2024; 1 page.

\* cited by examiner

MAGNETIC RESONANCE SCANNING METHOD AND SYSTEM AND COMPUTER-READABLE STORAGE MEDIUM

CROSS REFERENCE

The present application claims priority and benefit of Chinese Patent Application No. 202010242820.7 filed on Mar. 31, 2020, which in incorporated herein by reference in its entirety.

TECHNICAL FIELD

Embodiments disclosed in the present invention relate to medical imaging technologies, and more specifically, to a method and system for magnetic resonance scanning, and a computer-readable storage medium.

BACKGROUND

Magnetic resonance imaging (MRI), as a medical imaging modality, can obtain images of the human body without using X-rays or other ionizing radiation. MRI uses a magnet having a strong magnetic field to generate a static magnetic field B0. When a part to be imaged of a patient is positioned in the static magnetic field B0, nuclear spin associated with hydrogen nuclei (or other nuclides) in tissue of the part to be imaged is polarized, so that the tissue of the part to be imaged generates a longitudinal magnetization vector at a macroscopic level. After a radio-frequency field B1 intersecting the direction of the static magnetic field B0 is applied, the direction of rotation of protons changes so that the tissue of the part to be imaged generates a transverse magnetization vector at a macroscopic level. After the radio-frequency field B1 is removed, the transverse magnetization vector decays in a spiral manner until it is restored to zero. A free induction decay signal is generated during decay. The free induction decay signal can be acquired as a magnetic resonance signal, and a tissue image of the part to be imaged can be reconstructed based on the acquired signal.

To ensure the quality of magnetic resonance images, the static magnetic field B0 is generally required to have desirable uniformity. Magnetic resonance imaging has a variety of applications based on different imaging purposes. In some of the applications, the uniformity of the static magnetic field B0 is highly sensitive. In other words, in these applications, the non-uniformity of the static magnetic field B0 has a significant impact on the imaging effect. These applications include, for example, Echo Planar Imaging (EPI).

Shim calibration of the B0 field is usually performed during installation or periodic maintenance of a magnetic resonance device, and the calibrated static magnetic field B0 is considered to have high uniformity. However, during scanning of a patient, the dielectric effect caused by the patient's body usually causes different degrees of disturbance to the static magnetic field B0, which lowers the uniformity of the static magnetic field B0, thus affecting image quality. Such disturbance degree also changes with the position of the patient. As a result, during an imaging scan of the patient, an overall B0 field map at a current scan position needs to be obtained by scanning. However, when the supporting table carries the patient to move from the current scan position to another scan position, if the previously obtained overall B0 field map is still used, some image quality problems may arise since the overall B0 field map is less accurate; otherwise, an overall B0 field map at the another scan position needs to be obtained again by scanning, which increases the scanning time of the patient.

SUMMARY

An embodiment of the present invention provides a magnetic resonance scanning method, comprising:
when an imaging volume of an object is at a current position, performing a current imaging scan on the imaging volume based on a predicted overall B0 field map at the current position.

Optionally, the predicted overall B0 field map is obtained based on a background B0 field map and an overall B0 field map at a previous position of the imaging volume in a previous imaging scan.

Optionally, the performing a current imaging scan comprises: obtaining a shim value of the current imaging scan based on the predicted overall B0 field map at the current position.

Optionally, the performing a current imaging scan comprises: adjusting scan parameters of the current imaging scan based on the shim value of the current imaging scan.

Optionally, the overall B0 field map at the previous position is obtained based on a B0 field scan performed on the imaging volume in the previous imaging scan.

Optionally, the background B0 field map comprises a background B0 field map at the previous position and a background B0 field map at the current position, and the predicted overall B0 field map is predicted based on the background B0 field map at the current position, a disturbance B0 field map at the previous position, and the background B0 field map at the previous position, wherein the disturbance B0 field map at the previous position is obtained based on the overall B0 field map at the previous position and the background B0 field map at the previous position.

Optionally, the previous position comprises a first position of a preset layer of the imaging volume, the current position comprises a second position of the preset layer, the predicted overall B0 field map comprises an overall B0 field map at the second position, and the method further comprises the following steps to obtain the predicted overall B0 field map:
obtaining an overall B0 field map at the first position and a disturbance B0 field map at the first position when the preset layer of the imaging volume is at the first position, wherein the disturbance B0 field map at the first position is a difference between the overall B0 field map at the first position and a background B0 field map at the first position; and
predicting the overall B0 field map at the second position when the preset layer is at the second position, wherein the prediction is performed based on the disturbance B0 field map at the first position, the background B0 field map at the first position, and a background B0 field map at the second position.

Optionally, the predicting comprises:
obtaining correlation coefficients related to the preset layer, wherein the correlation coefficients are obtained based on the disturbance B0 field map at the first position and the background B0 field map at the first position;
correlating the correlation coefficients with the background B0 field map at the second position to obtain a disturbance B0 field map at the second position; and calculating the overall B0 field map at the second position based on the disturbance B0 field map at the second position and the background B0 field map at the second position.

Optionally, the predicting comprises: adding the disturbance B0 field map at the second position to the background B0 field map at the second position to obtain the overall B0 field map at the second position.

Optionally, the correlation coefficients comprise coefficients related to a linear relationship between the disturbance B0 field map at the first position and the background B0 field map at the first position.

Optionally, the correlation coefficients comprise a slope value in the linear relationship.

Optionally, the previous position further comprises a third position of the preset layer of the imaging volume, and the method further comprises the following steps to obtain the predicted overall B0 field map:

obtaining an overall B0 field map and a disturbance B0 field map at the third position when the preset layer is at the third position, wherein the disturbance B0 field map at the third position is a difference between the overall B0 field map at the third position and a background B0 field map at the third position; and predicting the overall B0 field map at the second position when the preset layer is at the second position, based on the disturbance B0 field map at the first position, the background B0 field map at the first position, the disturbance B0 field map at the third position, the background B0 field map at the third position, and the background B0 field map at the second position.

Optionally, the correlation coefficients are obtained based on the disturbance B0 field map at the first position, the background B0 field map at the first position, the disturbance B0 field map at the third position, and the background B0 field map at the third position, and the correlation coefficients further comprise an intercept value in the linear relationship.

Optionally, the obtaining the correlation coefficients comprises: obtaining a plurality of correlation coefficients related to a plurality of pixels of the preset layer based on a plurality of disturbance B0 field strengths of the disturbance B0 field map at the first position and a plurality of corresponding background B0 field strengths in the background B0 field map at the first position, and the predicting comprises: calculating a plurality of disturbance B0 field strengths at the second position based on the plurality of correlation coefficients and a plurality of corresponding background B0 field strengths in the background B0 field map at the second position, and calculating a plurality of overall B0 field strengths at the second position based on the plurality of background B0 field strengths at the second position and the plurality of disturbance B0 field strengths at the second position.

Optionally, the method further comprises:
performing low-pass filtering on the overall B0 field map at the previous position to obtain a reference background B0 field map; and
determining whether a difference between the reference background B0 field map and the background B0 field map is less than a first preset value, and if not, issuing alarm information.

Optionally, the method further comprises:
obtaining a standard background B0 field map related to a body part where the imaging volume is located;

calibrating the background B0 field map based on the standard background B0 field map to obtain a calibrated background B0 field map;
performing low-pass filtering on the overall B0 field map at the previous position to obtain a reference background B0 field map; and
determining whether a difference between the reference background B0 field map and the calibrated background B0 field map is less than a second preset value, and if so, using the calibrated background B0 field map as the background B0 field map to predict the overall B0 field map at the current position.

Optionally, the method further comprises: obtaining a standard background B0 field map related to the body part where the imaging volume is located, based on a plurality of reference background B0 field maps related to the body part where the imaging volume is located.

Optionally, the plurality of reference background B0 field maps related to the body part where the imaging volume is located are respectively obtained during a plurality of scans performed on the body part where the imaging volume is located.

Optionally, data fusion is performed on the plurality of reference background B0 field maps related to the body part where the imaging volume is located to obtain the standard background B0 field map.

Optionally, the method further comprises: updating the standard background B0 field map related to the body part where the imaging volume is located, based on the reference background B0 field map obtained by performing low-pass filtering on the overall B0 field map at the previous position.

Optionally, the reference background B0 field map obtained by performing low-pass filtering on the overall B0 field map at the previous position, the background B0 field map, the standard B0 field map, and the calibrated background B0 field map are all represented in a form of multi-order harmonic decomposition.

Optionally, the performing a current imaging scan on the imaging volume of the object further comprises:
executing an imaging scan sequence on the imaging volume to obtain an image of the imaging volume; and
correcting the image of the imaging volume based on the predicted overall B0 field map.

Another embodiment of the present invention further provides a magnetic resonance scanning system, comprising:
a scanner, comprising a table configured to carry an object to move, having a plurality of scan positions in a traveling direction of the table; and
a controller, configured to control the scanner to perform an imaging scan on an imaging volume of the object to obtain an image of the imaging volume, comprising performing the magnetic resonance scanning method according to any one of the embodiments described above.

Another embodiment of the present invention further provides a non-volatile computer-readable storage medium, for storing computer-readable instructions, wherein the computer-readable instructions are used for performing the magnetic resonance scanning method according to any one of the embodiments described above.

It should be understood that the brief description above is provided to introduce in simplified form some concepts that will be further described in the Detailed Description of the Embodiments. The brief description above is not meant to identify key or essential features of the claimed subject matter. The scope is defined uniquely by the claims that follow the detailed description. Furthermore, the claimed subject matter is not limited to implementations that solve any disadvantages noted above or in any section of the present disclosure.

BRIEF DESCRIPTION OF THE DRAWINGS

The present invention will be better understood by reading the following description of non-limiting embodiments with reference to the accompanying drawings, where.

DETAILED DESCRIPTION OF THE EMBODIMENTS

Figure 1:
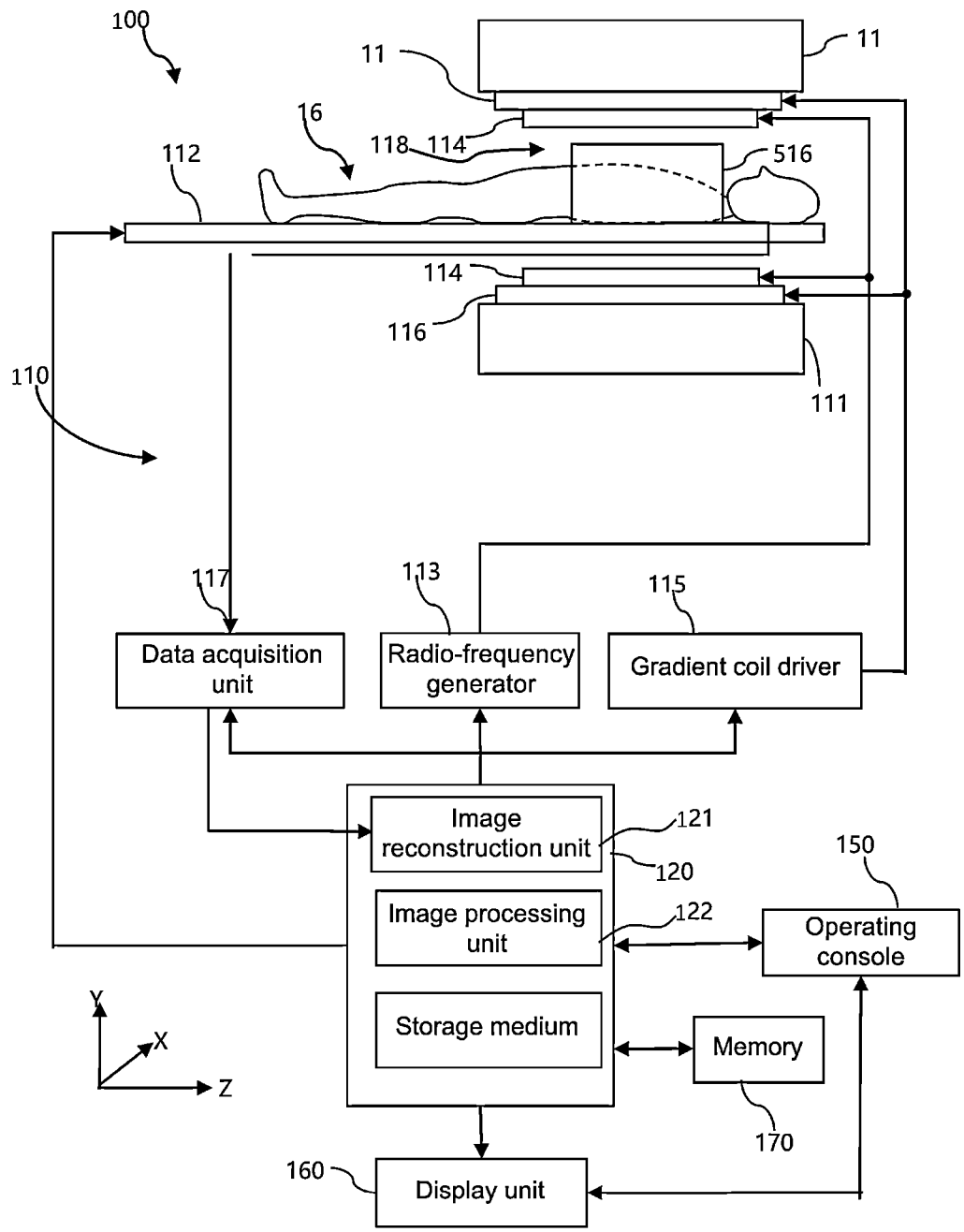
FIG. 1 is a schematic structural diagram of a magnetic resonance imaging system.

FIG. 1 is a schematic structural diagram of a magnetic resonance imaging system. The magnetic resonance imaging system 100 includes a scanner 110 and a controller 120. The controller 120 is coupled to the scanner 110 and configured to control the operation of the scanner 110, for example, control the scanner 110 to perform a scanning process on an object 16 to obtain image data of the object 16. The object 16 may include imaging tissue of a human body (for example, a patient).

Specifically, the controller 120 may send a sequence control signal to relevant components (such as a radio-frequency generator and a gradient coil driver that will be described below) of the scanner 110 through a sequence generator (not shown), so that the scanner 110 performs the preset scan sequence.

Those skilled in the art can understand that the "sequence" refers to a combination of pulses having specific amplitudes, widths, directions, and time sequences and applied when a magnetic resonance imaging scan is performed. The pulses may usually include, for example, a radio-frequency pulse and a gradient pulse. The radio-frequency pulse may include, for example, a radio-frequency transmit pulse for exciting protons in the human body to resonate, and the gradient pulse may include, for example, a slice selection gradient pulse, a phase encoding gradient pulse, and a frequency encoding gradient pulse.

In an example, the scanner 110 may include a main magnet assembly 111, a table 112, a radio-frequency generator 113, a radio-frequency transmitting coil 114, a gradient coil driver 115, a gradient coil assembly 116, and a data acquisition unit 117.

The main magnet assembly 111 usually includes an annular superconducting magnet defined in a housing. The annular superconducting magnet is mounted in an annular vacuum container. The annular superconducting magnet and the housing thereof define a cylindrical space, for example, a scanning chamber 118 shown in FIG. 1, surrounding the object 16. The main magnet assembly 111 generates a constant magnetic field, i.e., a B0 field, in a Z direction of the scanning chamber 118. Typically, a uniform portion of the B0 field is formed in a central region of the main magnet.

The table 112 is configured to carry the object 16, and travel in the Z direction to enter or exit the scanning chamber 118 in response to the control of the controller 120. For example, in an embodiment, an imaging volume of the object 16 may be positioned at a central region of the scanning chamber with uniform magnetic field strength so as to facilitate scanning imaging of the imaging volume of the object 16.

The magnetic resonance imaging system transmits a static magnetic pulse signal to the object 16 located in the scanning chamber using the formed B0 field, so that protons in resonant volumes in the body of the object 16 precess in an ordered manner to generate a longitudinal magnetization vector.

The radio-frequency generator 113 is configured to generate a radio-frequency pulse, for example, a radio-frequency excitation pulse, in response to a control signal of the controller 120. The radio-frequency excitation pulse is amplified (for example, by a radio-frequency power amplifier (not shown)) and then applied to the radio-frequency transmitting coil 114, so that the radio-frequency transmitting coil 114 emits to the object 16 a radio-frequency field B1 orthogonal to the B0 field to excite nuclei in the aforementioned resonant volumes, and generate a transverse magnetization vector.

The radio-frequency transmitting coil 114 may include, for example, a body coil disposed along an inner circumference of the main magnet, or a head coil dedicated to head imaging. The body coil may be connected to a transmitting/receiving (T/R) switch (not shown). The transmitting/receiving switch is controlled so that the body coil can be switched between a transmitting mode and a receiving mode. In the receiving mode, the body coil may be configured to receive a magnetic resonance signal from the object 16.

After the end of the radio-frequency excitation pulse, a free induction decay signal, namely, a magnetic resonance signal that can be acquired, is generated in the process that the transverse magnetization vector of the object 16 is gradually restored to zero.

The gradient coil driver 115 is configured to provide a suitable current/power to the gradient coil assembly 116 in response to a gradient pulse control signal or a shimming control signal sent by the controller 120.

The gradient coil assembly 116, on one hand, forms a varying magnetic field in an imaging space so as to provide three-dimensional position information to the magnetic resonance signal, and on the other hand, generates a compensating magnetic field of the B0 field to shim the B0 field.

The gradient coil assembly 116 may include three gradient coils. The three gradient coils are respectively configured to generate magnetic field gradients inclined to three spatial axes (for example, X-axis, Y-axis, and Z-axis) perpendicular to each other. More specifically, the gradient coil assembly 116 applies a magnetic field gradient in a slice selection direction (Z direction) so as to select a layer in the imaging volume. Those skilled in the art understand that the layer is any one of a plurality of two-dimensional slices distributed in the Z direction in the three-dimensional imaging volume. When the imaging is scanned, the radio-frequency transmitting coil 114 transmits a radio-frequency excitation pulse to the layer of the imaging volume and excites the layer. The gradient coil assembly 116 applies a magnetic field gradient in a phase encoding direction (Y direction) so as to perform phase encoding on a magnetic resonance signal of the excited layer. The gradient coil assembly 116 applies a gradient field in a frequency encoding direction of the object 16 so as to perform frequency encoding on the magnetic resonance signal of the excited layer.

The data acquisition unit 117 is configured to acquire the magnetic resonance signal (for example, received by the body coil or a surface coil) in response to a data acquisition control signal of the controller 120. In an embodiment, the data acquisition unit 117 may include, for example, a radio-frequency preamplifier, a phase detector, and an analog/digital converter, where the radio-frequency preamplifier is configured to amplify the magnetic resonance signal, the phase detector is configured to perform phase detection on the amplified magnetic resonance signal, and the analog/digital converter is configured to convert the phase-detected magnetic resonance signal from an analog signal to a digital signal.

The controller 120 may communicate with an operating console 150. The operating console 150 may include user input devices, such as a keyboard and a mouse. The controller 120 may control various components of the scanner 110 to perform corresponding operations in response to a control command of a user generated based on the operating console 150 or an operation panel/button provided on the housing of the main magnet.

The controller 120 may include an image reconstruction unit 121 and an image processing unit 122. The reconstruction unit 121 is configured to reconstruct an image of the imaging volume of the object 16 based on the digitized magnetic resonance signal. The image processing unit 122 may be configured to perform any desired image processing, for example, image correction, on the reconstructed image.

The operating console 150 is connected to the display unit 160 that may display an operation interface and various data or images generated in the data processing process.

The controller 120 may include a computer and a storage medium, where a predetermined control program and a data processing program to be executed by the computer are recorded on the storage medium. For example, a program for implementing a main magnetic field evaluation method and a gradient field evaluation method according to embodiments of the present invention may be stored on the storage medium. The storage medium may include, for example, a ROM, a floppy disk, a hard disk, an optical disk, a magneto-optical disk, a CD-ROM, or a non-volatile memory card.

The imaging system shown in FIG. 1 may further include a memory 170 that may be configured to store information such as patient information, scanning protocols, and system parameters. The system parameters may include, for example, a background B0 field map. The background B0 field map may be pre-obtained by a variety of methods and pre-stored in the memory 170 before scanning imaging is performed on the object 16. For example, during installation, calibration, or daily maintenance of the magnetic resonance imaging device, the background B0 field map may be obtained by imaging a body mold and calculation based on imaging data, or a background B0 field may be measured by a field strength measuring device.

Since magnetic resonance imaging involves imaging of an imaging volume of a human body, at least a background B0 field strength distribution, namely, a background B0 field map, in a three-dimensional space where the imaging volume is located needs to be pre-stored before an imaging scan. The background B0 field map includes background B0 field maps at a plurality of positions (for example, a previous position, a current position, a first position and a third position in the previous positions, and a second position in the current position that will be described below) in the Z direction, namely, B0 field strength distributions in a plurality of X-Y planes. A position in the Z direction of each X-Y plane may be the first position, the second position, or the third position described below. Therefore, the "first position", the "second position", and the "third position" described below may respectively include a plurality of positions distributed in the X-Y plane in a field of view (FOV).

Similarly, the overall B0 field map, disturbance B0 field map, reference background B0 field map, standard background B0 field map, and calibrated background B0 field map involved in the embodiments of the present invention may also include the B0 field maps in the three-dimensional space, which further include B0 field maps at a plurality of positions in the Z direction.

Scans at the plurality of positions may be involved in the process of the imaging scan performed on the imaging volume of the object. For example, a complete imaging scan may include a pre-scan and a formal scan. A positioning image may be obtained by performing the pre-scan when the imaging volume of the object 16 is positioned at an initial position (for example, a Landmark position). A field of view (FOV) in the formal scan may be further determined based on the positioning image, and then precise positioning information of the imaging volume in the formal scan can be determined. Thus, prior to the formal scan, the movable table is controlled, based on the precise positioning information, to travel in the Z direction to position the imaging volume again, for example, align a center of the determined FOV with a scan center. For another example, a complete imaging scan may include a plurality of scans for a plurality of positions of body parts. For example, first, an area below eyes of the head is imaged, and then, a forehead area of the head is imaged. FOVs in the two imaging processes are different. Thus, after one scan is completed, the movable table is controlled to travel in the Z direction based on the FOV in the next scan.

In the embodiments of the present invention, in order to achieve better image quality in each imaging process, an overall B0 field map is considered instead of just considering a background B0 field map (namely, the pre-stored B0 field map described above) in the determination of a B0 field. The overall B0 field map further includes a disturbance B0 field map generated by disturbance to the background B0 field map that is caused by the body of the object 16, so as to obtain a more accurate B0 field map, thereby avoiding image quality problems, for example, image distortion, caused by B0 field disturbance during subsequent image reconstruction or post-processing.

Moreover, in order to save the scanning time, a current imaging scan is performed directly based on a predicted overall B0 field map at the current position without the need to perform a B0 field scan in order to obtain the overall B0 field map, thereby saving the scanning time.

Various specific embodiments of the magnetic resonance scanning method provided in the present invention will be described in detail below.

First Embodiment

Figure 2:
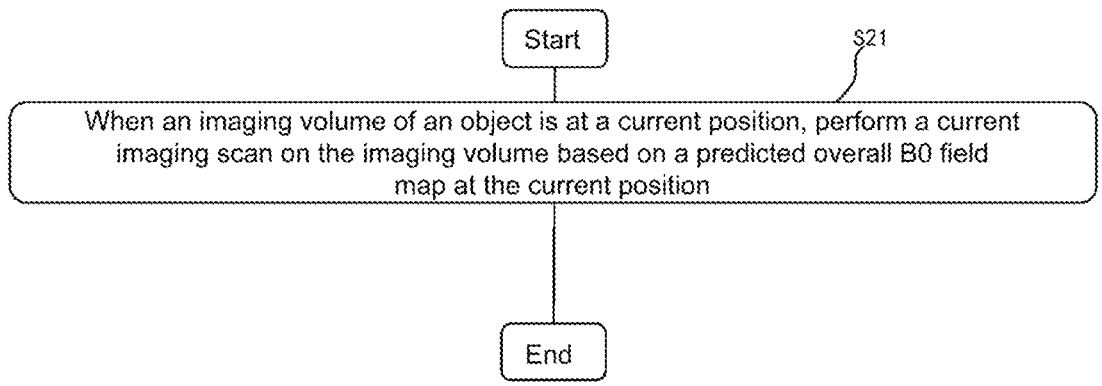
FIG. 2 is a flowchart of a magnetic resonance scanning method according to a first embodiment of the present invention.

FIG. 2 is a flowchart of a magnetic resonance scanning method according to the first embodiment of the present invention. As shown in FIG. 2, step S21: when an imaging volume of an object is at a current position, a current imaging scan on the imaging volume is performed based on a predicted overall B0 field map at the current position.

In an implementation, the predicted overall B0 field map is obtained based on a background B0 field map and an overall B0 field map at a previous position of the imaging volume in a previous imaging scan. In this manner, an overall B0 field map at a next position or a current position is predicted directly based on a scanned overall B0 field map at a previous position, without the need to perform a B0 field scan again in order to obtain the overall B0 field map, thereby saving the scanning time.

Those skilled in the art can understand that the "imaging volume" may be a three-dimensional area imaged in the body of the object when an imaging scan is performed, where the area may usually be determined by setting scan parameters. The imaging volume may usually include a plurality of volume layers, namely, "layers" or "X-Y planes," sequentially distributed in a Z direction.

The current position described above may be, for example, a position range of the imaging volume when a formal scan is performed, and may include a position of each layer of the imaging volume in the formal scan, for example, the second position described below. The previous position described above may be, for example, a position range of the imaging volume when a pre-scan is performed, and may include a position of each layer described above in the pre-scan, for example, the first position that will be described below.

As described above, the aforementioned background B0 field map is pre-stored in the magnetic resonance imaging system and includes background B0 field maps distributed throughout a three-dimensional imaging space (for example, a spherical space or a space of a similar shape). The three-dimensional imaging space may include a plurality of positions in the Z direction and may include the previous position, current position, first position, second position and/or third position described in the embodiments of the present invention. Accordingly, it can be considered that the "background B0 field map" includes a background B0 field map at the current position and a background B0 field map at the previous position; the background B0 field map at the current position may further include a background B0 field map at the second position; the background B0 field map at the previous position may further include a background B0 field map at the first position and/or a background B0 field map at the third position.

In an embodiment, the overall B0 field map at the previous position is obtained based on a B0 field scan performed on the imaging volume in the previous imaging scan.

The overall B0 field map reflects the spatial distribution of a B0 field. Since the magnitude of the overall B0 field affects the angular velocity of deflection of a longitudinal magnetization vector of protons, and then the field strength of the overall B0 field has a specific functional relationship with the phase change of a magnetic resonance signal over time, the overall B0 field map at the same position may be obtained through differences between magnetic resonance signals acquired at the same position at different moments.

Based on the above principles, in an implementation of the present invention, the overall B0 field map at the previous position may be obtained in the following manner: two sets of image data of the imaging volume obtained when the previous imaging scan is performed are obtained, where the two sets of image data respectively have different phase information, and an overall B0 field map related to the first position is calculated based on a phase difference between the two sets of image data. For example, various components of the scanner 110 execute a B0 field scan sequence in response to a control signal of the controller 120 to obtain the aforementioned two sets of image data. The B0 field scan sequence may be executed as part of an imaging scan sequence, or may be executed before or after the imaging scan is completed. When the B0 field scan sequence is executed, image data having B0 field strength information is obtained, which is usually used for determination, setting, and the like of system parameters. When the imaging scan sequence is executed, magnetic resonance image data of different tissue of the human body is obtained, which is usually used for clinical diagnosis. A variety of B0 field scan sequences and imaging scan sequences exist in the prior art based on different clinical applications, and will not be described herein again.

In step S21, the procedure to perform the current imaging scan may include: obtaining a shim value of the current imaging scan based on the predicted overall B0 field map at the current position, and further adjusting scan parameters of the current imaging scan based on the obtained shim value. Specifically, when the current imaging scan is performed, appropriate scan parameters, for example, a gradient current and a central frequency, related to the obtained shim value may be selected, which will also be described in a sixth embodiment.

Specifically, the predicted overall B0 field map is predicted based on the background B0 field map at the current position, a disturbance B0 field map at the previous position, and the background B0 field map at the previous position, where the disturbance B0 field map at the previous position is obtained based on the overall B0 field map at the previous position and the background B0 field map at the previous position. For example, the disturbance B0 field map at the previous position may be obtained by subtracting the background B0 field map at the previous position from the overall B0 field map at the previous position.

It should be noted that the predicted overall B0 field map at the current position may include an overall B0 field map at a position of each layer, or may include overall B0 field maps at positions of some layers.

Second Embodiment

Figure 3:
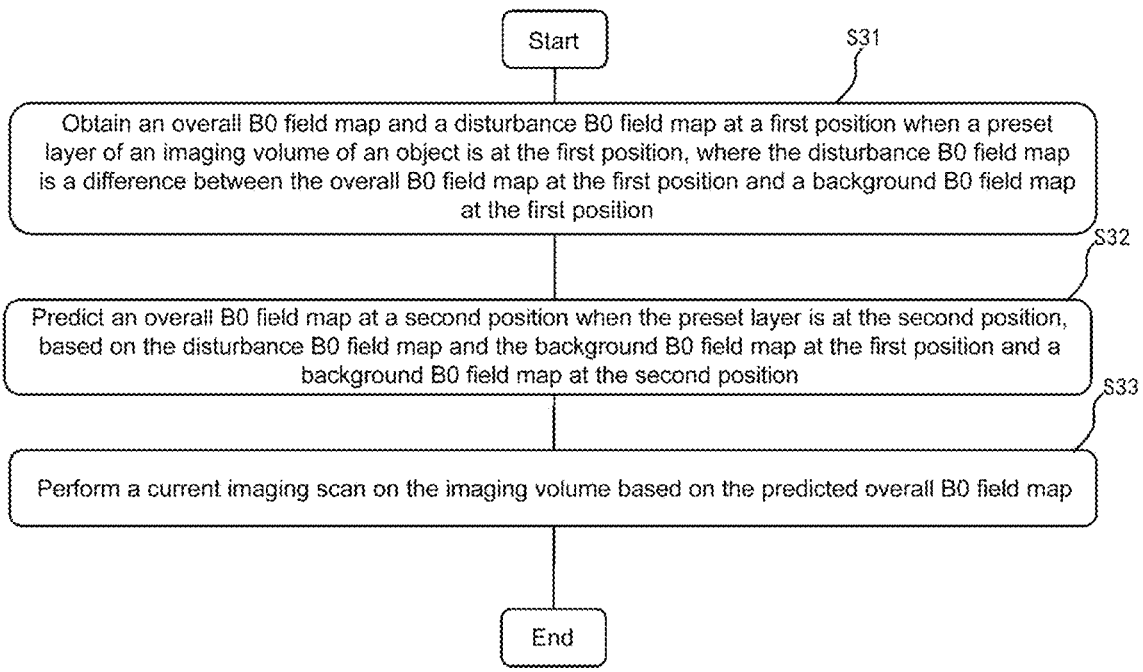
FIG. 3 is a flowchart of a magnetic resonance scanning method according to a second embodiment of the present invention.

FIG. 3 is a flowchart of a magnetic resonance scanning method according to the second embodiment of the present invention. As shown in FIG. 3, the method further includes step S33, which is similar to step S21. The method in this embodiment further includes steps S31 and S32 to obtain the predicted overall B0 field map.

In step S31, an overall B0 field map and a disturbance B0 field map at a first position are obtained when a preset layer of an imaging volume of an object is at the first position. The disturbance B0 field map at the first position may be a disturbance B0 field map caused by the object's body, and is a difference between the overall B0 field map at the first position and a background B0 field map at the first position.

In step S31, data at the first position may be obtained directly in a background B0 field to obtain the background B0 field map at the first position.

When the imaging volume is at a previous position, a position of the preset layer of the imaging volume is a first position. An overall B0 field map distributed in a three-dimensional space may be obtained by executing a B0 field scan sequence on the imaging volume. The overall B0 field map may include an overall B0 field map throughout the three-dimensional imaging space, or may include an overall B0 field map at one or a plurality of Z-axis positions in the three-dimensional imaging space. Specifically, the overall B0 field map may include an "overall B0 field map at the previous position" or an "overall B0 field map at the first position". In step S21, data at the first position may be obtained in the "overall B0 field map at the previous position" to obtain the overall B0 field map at the first position.

Similarly, when the imaging volume is at another previous position, the position of the preset layer of the imaging volume is a third position. An overall B0 field map distributed in a three-dimensional space obtained by executing a B0 field scan sequence on the imaging volume may include an "overall B0 field map at the previous position" or an "overall B0 field map at the third position".

In step S32, an overall B0 field map at a second position is predicted when the preset layer is at the second position, based on the disturbance B0 field map at the first position, the background B0 field map at the first position, and a background B0 field map at the second position.

When the imaging volume is at the current position, the position of the preset layer of the imaging volume is a second position, and an overall B0 field map at one or a plurality of second positions predicted based on this embodiment may be used as the "overall B0 field map at the current position".

As an example, the preset layer of the imaging volume may be a central layer determined in the imaging volume, the second position may be a position aligned with a scan center (or magnet center) of the magnetic resonance imaging system, and when a scan at the second position is performed, the central layer may be located at the second position. The first position may be a position of the central layer in the Z direction with respect to the scan center (or magnet center) when a pre-scan is performed on the imaging volume.

Like the obtaining of the overall B0 field map at the first position, in step S32, data at the second position may be obtained directly in the background B0 field to obtain the background B0 field map at the second position.

Any of the plurality of volume layers of the imaging volume may be the "preset layer" described in this embodiment. That is, when an overall B0 field map at any position in a scan needs to be predicted, it is only needed to predetermine the specific volume layer at the position in the scan. When overall B0 field maps related to a plurality of layers need to be obtained, each of the layers may be used as the preset layer to perform steps S31 and S32.

Figure 4:
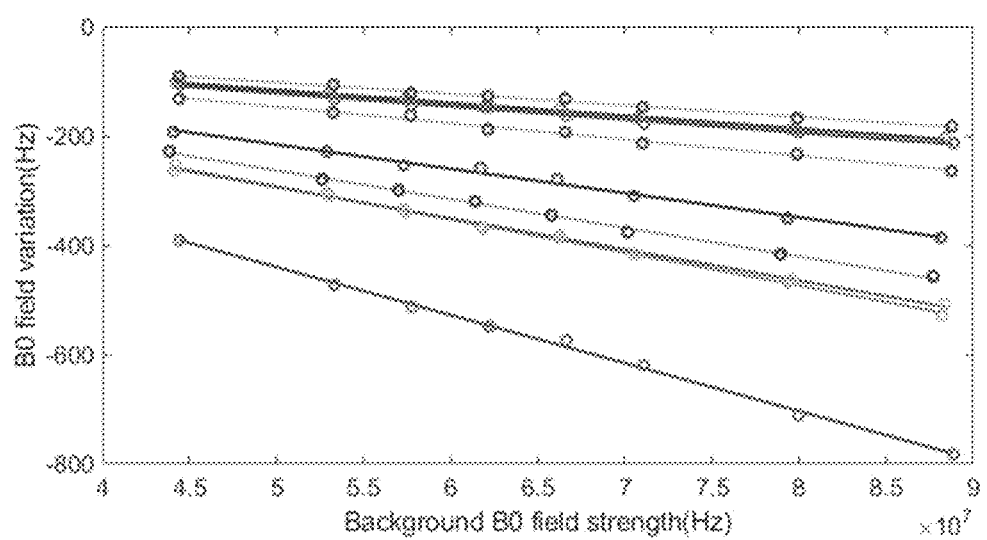
FIG. 4 is a variation diagram of disturbance B0 field strengths at a plurality of positions acquired when an imaging volume is placed at different B0 field strengths.

FIG. 4 is a variation diagram of disturbance B0 field strengths at a plurality of positions acquired when an imaging volume is placed at different B0 field strengths. The inventor of the present invention first made a bold assumption that a disturbance B0 field strength and a background B0 field strength at the same position have a specific relationship, and thus conducted a large number of experiments to verify that they have the linear relationship shown in FIG. 3. Such experiments may include, for example, placing an imaging volume in a strong magnetic field having strong uniformity for magnetic resonance scanning or magnetic resonance simulation scanning, obtaining overall B0 field strengths at a plurality of acquisition points by the aforementioned method, then obtaining disturbance B0 field strengths at these acquisition points (an overall B0 field strength minus a background B0 field strength at a corresponding position), and finally establishing a relationship diagram of the disturbance B0 field strength and the background B0 field strength. The plurality of lines in FIG. 4 correspond to a plurality of acquisition points (for example, a plurality of pixels of the imaging volume). Although FIG. 4 only shows data of a few acquisition points, data analysis may be performed on more acquisition points in practice. The horizontal axis in FIG. 4 represents the background B0 field strength, and the longitudinal axis represents the disturbance B0 field strength. The disturbance B0 field strength and the background B0 field strength have the following relationship:

$$\Delta B(x,y,z)=k(x,y,z) \cdot B0(x,y,z)+b(x,y,z) \qquad (1).$$

In the above formula (1), $\Delta B(x,y,z)$ is the disturbance B0 field strength, and $B0(x,y,z)$ is the background B0 field strength. $k(x,y,z)$ and $b(x,y,z)$ are respectively constants, where $k(x,y,z)$ represents a slope, $b(x,y,z)$ represents an intercept, and $(x,y,z)$ represents three-dimensional components in each data value.

Figure 5:
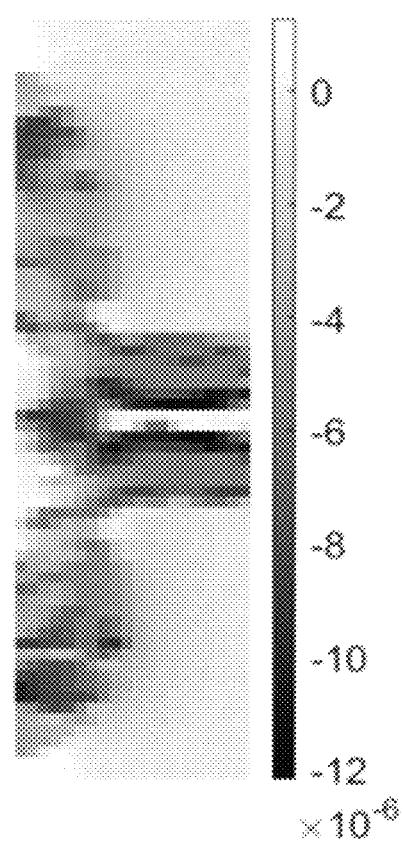
FIG. 5 and FIG. 6 illustrate a k-value component and a b-value component in a disturbance B0 field map in the field of view.
Figure 6:
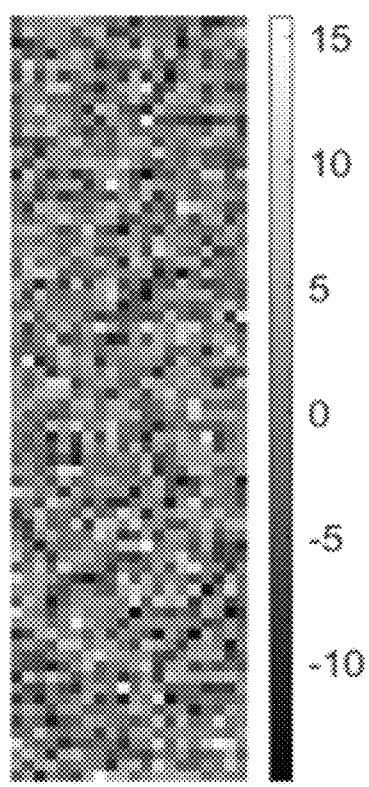

A k value and a b value of each pixel may be calculated based on a known overall B0 field map and a known background B0 field map in a field of view (for example, obtained by executing a B0 field scan sequence). FIG. 5 and FIG. 6 illustrate a k-value component and a b-value component in a disturbance B0 field map in the field of view. It can be known from FIG. 5 and FIG. 6 that the b-value component contains a lot of background noise. The background noise has less effect on the prediction result of the overall B0 field and is negligible. Thus, a relationship between a disturbance B0 field strength related to each pixel in the disturbance B0 field map and a background B0 field strength related to the pixel may be predefined as the linear relationship shown in the following formula (2), namely:

$$\Delta B(x,y,z)=k(x,y,z) \cdot B0(x,y,z) \qquad (2).$$

Such a relationship is applicable to each pixel in a B0 field map at each position. That is, a relationship between a disturbance B0 field strength related to each pixel in the disturbance B0 field map at the first position and a background B0 field strength related to the corresponding pixel in the background B0 field map at the first position may be preset as the aforementioned linear relationship.

Thus, in step S32, the procedure to predict an overall B0 field map at a second position when the preset layer is at the second position may include the following three substeps:
the first substep: correlation coefficients related to the preset layer is obtained based on the disturbance B0 field map at the first position and the background B0 field map at the first position. Optionally, the correlation coefficients may include coefficients related to a linear relationship between the disturbance B0 field map at the first position and the background B0 field map at the first position. Further, the correlation coefficients include a slope value in the linear relationship, for example, the k value.

In the first substep, a plurality of correlation coefficients, for example, a plurality of k values, related to a plurality of pixels of the preset layer may be obtained based on a plurality of disturbance B0 field strengths of the disturbance B0 field map at the first position and a plurality of corresponding background B0 field strengths in the background B0 field map at the first position. The second substep: the correlation coefficients are correlated with the background B0 field map at the second position to obtain a disturbance B0 field map at the second position. For example, a disturbance B0 field strength at the second position related to each pixel of the preset layer is calculated based on the background B0 field map at the second position and the correlation coefficients related to each pixel of the preset layer. Specifically, a field strength at each position in the background B0 field map at the second position may be multiplied by a corresponding k value to obtain the disturbance B0 field map at the second position when the preset layer is at the second position.

The third substep: the overall B0 field map at the second position (when the preset layer is at the second position) is calculated based on the disturbance B0 field map at the second position and the background B0 field map at the second position. For example, the disturbance B0 field map at the second position and the background B0 field map at the second position are added up to obtain the overall B0 field map at the second position.

Specifically, a plurality of disturbance B0 field strengths at the second position may be calculated based on the plurality of correlation coefficients and a plurality of corresponding background B0 field strengths in the background B0 field map at the second position, and a plurality of overall B0 field strengths at the second position may be calculated based on the plurality of background B0 field strengths at the second position and the plurality of disturbance B0 field strengths at the second position.

In different system configurations, parameter settings or scanning environments, the disturbance B0 field and the background B0 field may have other relationships than the linear relationship, but they all fall within the protection scope of the present invention as long as the disturbance B0 field map or the overall B0 field map can be predicted based on such relationships based on the design concept of the present invention.

Third Embodiment

As described above, the background B0 field map is pre-obtained and pre-stored. The actual background B0 field map may drift over time, which lowers the accuracy of the overall B0 field map predicted based on the background B0 field. In order to solve the problem, the third embodiment of the present invention further evaluates the accuracy of the background B0 field based on any of the aforementioned embodiments, so as to ensure the accuracy of the estimated overall B0 field map.

Figure 7:
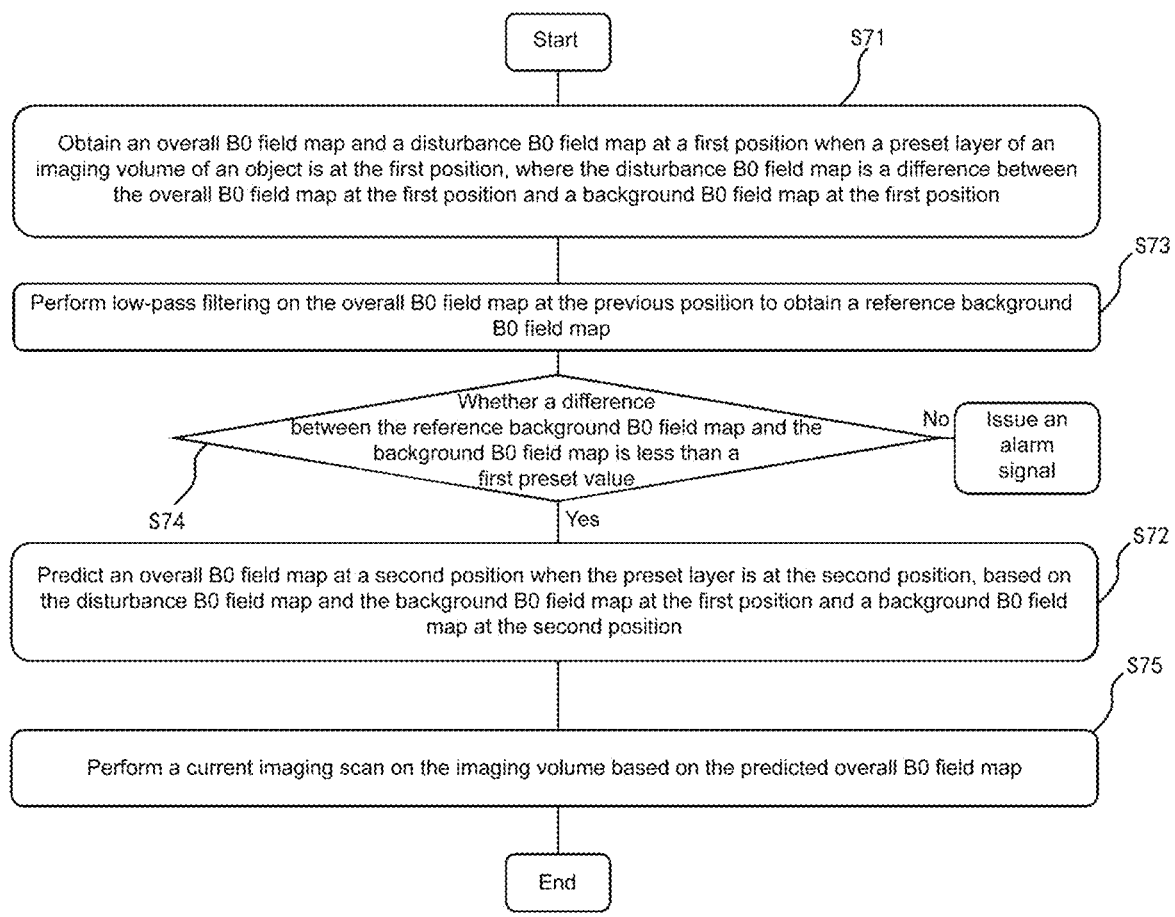
FIG. 7 is a flowchart of a magnetic resonance scanning method according to a third embodiment of the present invention.

FIG. 7 is a flowchart of a magnetic resonance scanning method according to the third embodiment of the present invention. As shown in FIG. 7, the third embodiment includes steps S71, S72, S73, S74, and S75, where steps S71, S72, and S75 are respectively similar to the aforementioned steps S31, S32, and S21.

In step S73: low-pass filtering is performed on an overall B0 field map at a previous position to obtain a reference background B0 field map. As described above, the overall B0 field map at the previous position may include: an overall B0 field map in a three-dimensional space where an imaging volume is located, when the imaging volume is at the previous position (or when the preset layer is at a first position). A disturbance B0 field caused by an object's body is filtered out by low-pass filtering, so as to obtain a reference background B0 field map close to an actual background B0 field map.

In step S74: it is determined whether a difference between the reference background B0 field map and the background B0 field map is less than a first preset value, and if not, alarm information is issued. In this step, it is determined whether the reference background B0 field map and the background B0 field map are close enough to analyze whether the background B0 field map drifts. If the difference is excessively large, it indicates that the background B0 field map is less accurate; at this time, alarm information related to the background B0 field map may be issued. The background B0 field map may be calibrated and updated based on the alarm information. Such update may be performed after the scan ends or may be performed in real time during the scan.

In an implementation, in comparing the reference background B0 field map and the background B0 field map, harmonic decomposition may be separately performed on them before comparison. For example, the reference background B0 field map may be decomposed as $H1=a1+b1*x+c1*y+d1*x*x+e1*x*y+f1*y*y$ (3), and the background B0 field map may be decomposed as $H2=a2+b2*x+c2*y+d2*x*x+e2*x*y+f2*y*y$ (4), where x and y in formulas (3) and (4) respectively represent components in an X direction and a Y direction in the B0 field map, a1 and a2 are fundamental components, and b1, b2, c1, c2, d1, d2, e1, e2, f1, and f2 are respectively harmonic coefficients. In step S74, differences may be calculated for the components in formulas (3) and (4) to determine whether the reference background B0 field map and the background B0 field map are close enough.

In an implementation, steps S73 and S74 may be performed between step S71 and step S72.

If the reference background B0 field map is close enough to the pre-stored background B0 field map, the magnetic resonance imaging system can be controlled to work according to the conventional procedure.

Fourth Embodiment

In the fourth embodiment of the present invention, the background B0 field map may be calibrated in real time so that a more accurate overall B0 field map can be estimated. It is found through research that when low-pass filtering is performed on overall B0 field maps obtained by scanning different body parts, obtained reference background B0 field maps after filtering are different due to different body parts. This may be because different parts of the body have different low-order terms, and the difference may be caused by different configurations of the body parts. For example, the head that is symmetric on left and right sides and the abdomen that is not symmetric on left and right sides cause different low-order terms. In this embodiment, first, corresponding standard background B0 field maps may be obtained for different body parts, and a corresponding standard background B0 field map may be selected, based on a body part where the current imaging volume is located, to calibrate the background B0 field map.

Figure 8:
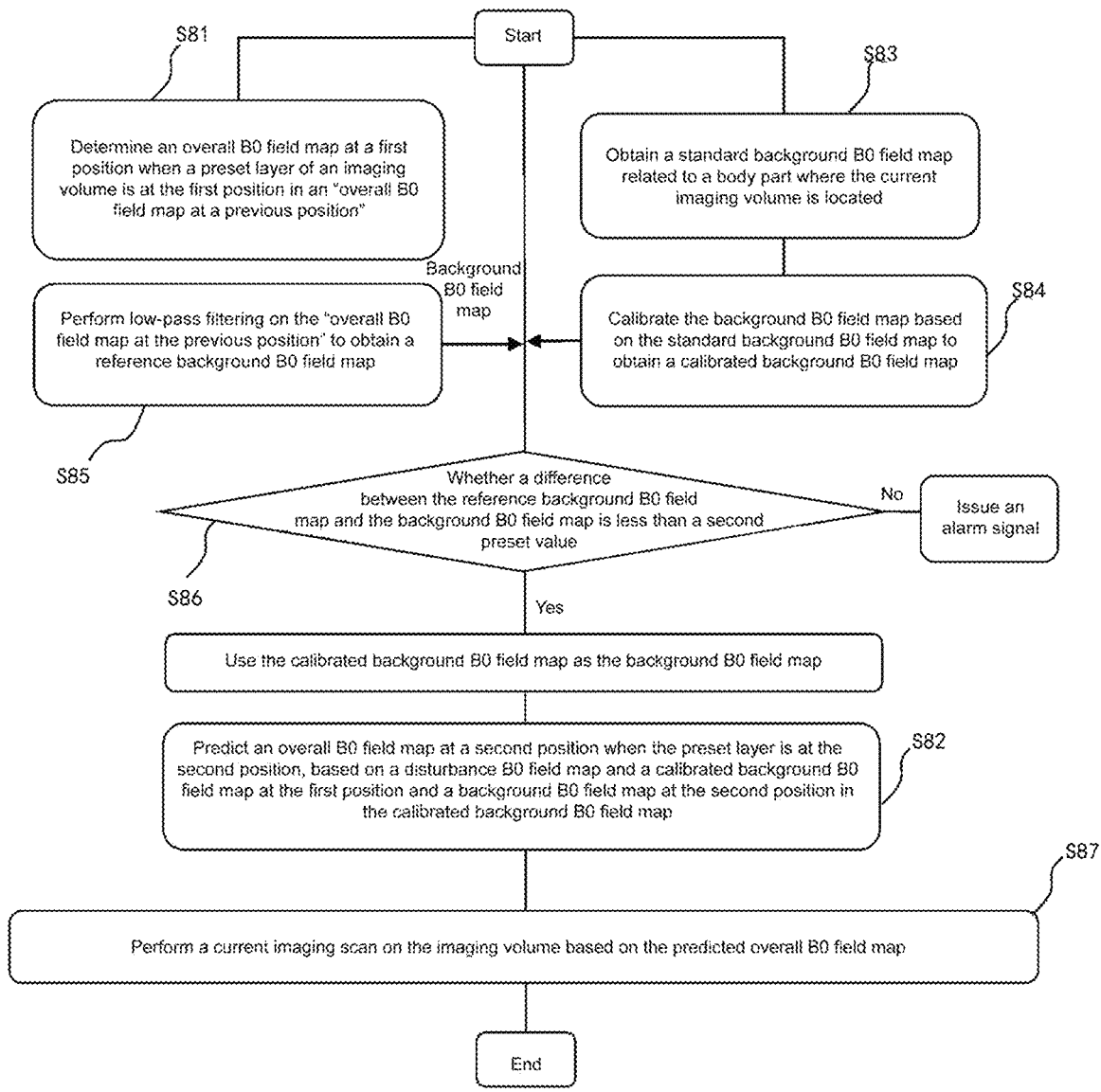
FIG. 8 is a flowchart of a magnetic resonance scanning method according to a fourth embodiment of the present invention.

FIG. 8 is a flowchart of a magnetic resonance scanning method according to the fourth embodiment of the present invention. As shown in FIG. 8, the third embodiment includes steps S81, S82, S83, S84, S85, S86, and S87, where steps S81, S82, and S87 are respectively similar to the aforementioned steps S31, S32, and S21. Especially in step S81, an overall B0 field map at a first position may be determined in an overall B0 field map at a previous position, so as to "obtain an overall B0 field map and a disturbance B0 field map at a first position when a preset layer is at the first position". In an implementation, steps S83 to S86 may be performed between steps S81 and S82.

In step S83: a standard background B0 field map related to a body part where a current imaging volume is located is obtained. The standard background B0 field map may be pre-stored in a memory (for example, the memory 170) of the magnetic resonance imaging system. Moreover, in this step, the standard background B0 field map related to the body part (or any imaging volume in the body part) may be obtained based on a plurality of pre-obtained reference background B0 field maps related to the body part. The plurality of reference background B0 field maps related to the body part are respectively obtained in a plurality of scans performed on the body part, which may be obtained based on historical data of magnetic resonance scanning. In an implementation, data fusion is performed on the plurality of reference background B0 field maps related to the body part to obtain the standard background B0 field map related to the body part.

Using the head as an example, a plurality of overall B0 field maps related to the head may be obtained in a plurality of scans performed on heads (for example, of patients having different identities), and a different imaging volume in the head may be set in each scan. A plurality of corresponding reference background B0 field maps related to the head may be obtained by performing low-pass filtering on the plurality of overall B0 field maps related to the head. Data fusion such as averaging or median calculation is performed on the plurality of reference background B0 field maps related to the head to obtain the standard background B0 field map related to the head. Thus, in step S83, if the currently scanned body part is also the head, the aforementioned standard background B0 field map related to the head may be retrieved to realize real-time calibration of a background B0 field map in subsequent steps.

In step S84: the background B0 field map is calibrated based on the standard background B0 field map to obtain a calibrated background B0 field map. In an implementation, data fusion is performed on the standard background B0 field map and the background B0 field map to obtain a calibrated background B0 field map. Such data fusion may include, for example, separately performing harmonic decomposition on the standard background B0 field map and the background B0 field map to obtain their respective plurality of components, and corresponding components in the standard background B0 field map and the background B0 field map are added up to obtain a calibrated background B0 field map represented in the form of harmonic decomposition. Different body parts cause a B0 field variation (the plurality of components may represent the variation). After low-pass filtering is performed on a large number of overall B0 field maps of one body part to filter out high-order components and then data fusion such as averaging is performed on remaining low-order components, B0 field low-order components caused by the body part can be obtained. When each low-order component thereof is added to the corresponding component of the background B0 field, the obtained calibrated background B0 field map is considered close to the reference background B0 field map.

In step S85: low-pass filtering is performed on the overall B0 field map at the previous position to obtain a reference background B0 field map. Step S85 is similar to step S73, and will not be described herein again.

In step S86: it is determined whether a difference between the reference background B0 field map and the calibrated background B0 field map is less than a second preset value, and if so, use the calibrated background B0 field map as the background B0 field map to perform step S82; that is, the overall B0 field map at a second position when the preset layer is at the second position is predicted based on the disturbance B0 field map at the first position, the calibrated background B0 field map, and a background B0 field map at the second position in the calibrated background B0 field map, so as to obtain a predicted overall B0 field map at a current position. The second preset value defines a threshold of the difference between the reference background B0 field map and the calibrated background B0 field map, and if the threshold is exceeded, it is considered that the obtained calibrated background B0 field map is less accurate; otherwise, the calibrated background B0 field map is considered as reliable calibrated data, and the overall B0 field can be predicted based on the calibrated data rather than the original background B0 field map. In this step, differences may be separately calculated for various components of the reference background B0 field map after harmonic decomposition and corresponding components of the calibrated background B0 field map, and these differences are subjected to data processing before comparison with the second preset value. The second preset value and the first preset value may be the same or different.

Fifth Embodiment

Figure 9:
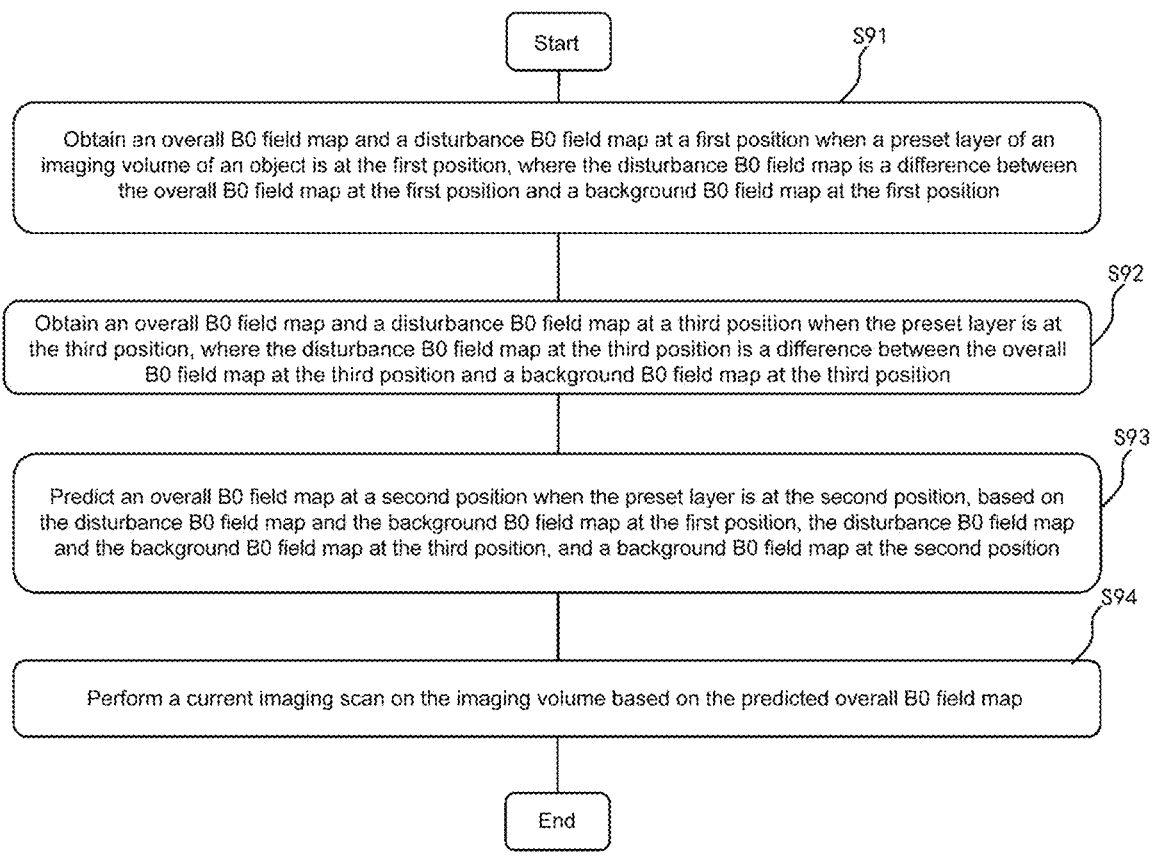
FIG. 9 is a flowchart of a magnetic resonance scanning method according to a fifth embodiment of the present invention.

FIG. 9 is a flowchart of a magnetic resonance scanning method according to the fifth embodiment of the present invention. As shown in FIG. 9, the method includes steps S91, S92, S93, and S94, where step S91 is similar to step S31, and step S94 is similar to step S21. The fifth embodiment of the present invention is similar to any of the embodiments described above. The difference lies in that in this embodiment, a predefined linear relationship between a disturbance B0 field strength and a background B0 field strength (for example, formula (1) above) is used to predict an overall B0 field map at another position by scanning overall B0 field maps at two positions.

In step S92: an overall B0 field map and a disturbance B0 field map at a third position when a preset layer is at the third position are obtained, where the disturbance B0 field map at the third position is a difference between the overall B0 field map at the third position and a background B0 field map at the third position in background B0 field maps.

In step S93: an overall B0 field map at a second position when the preset layer is at the second position is predicted based on the disturbance B0 field map at the first position, the background B0 field map at the first position, the disturbance B0 field map at the third position, the background B0 field map at the third position, and a background B0 field map at the second position.

In this embodiment, correlation coefficients, for example, a k value (slope) and a b value (intercept), related to each pixel may be obtained through data at the first position and data at the third position according to the relationship described in formula (1) (or any other flexible mathematical expression), and used together with the background B0 field map at the second position for calculation to obtain a disturbance B0 field map at the second position, and then obtain the overall B0 field map at the second position.

Specifically, the "predicting an overall B0 field map at a second position when the preset layer is at the second position" includes:

calculating at least two correlation coefficients, for example, the aforementioned k value and b value, related to each pixel of the preset layer according to a predefined linear relationship between a disturbance B0 field value related to each pixel of the preset layer in the disturbance B0 field map and a background B0 field strength related to the pixel and based on the disturbance B0 field map and the background B0 field map at the first position as well as the disturbance B0 field map and the background B0 field map at the third position;

calculating a disturbance B0 field value at the second position related to each pixel of the preset layer based on the background B0 field map at the second position and the two correlation coefficients related to each pixel of the preset layer; and calculating the overall B0 field map at the second position when the preset layer is at the second position, based on the disturbance B0 field value at the second position related to each pixel of the preset layer and the background B0 field map at the second position.

Such an embodiment can be applied to, for example, an imaging method sensitive to b values.

The above embodiment describes the magnetic resonance scanning method in the present invention. An overall B0 field map at a scan position where a scan is to be performed is obtained, so that a B0 field scan sequence does not need to be added in an imaging sequence, thereby saving the scanning time. Moreover, in the embodiment of the present invention, overall B0 field maps may be predicted for a plurality of "preset layers". In the above embodiment, the accuracy of the background B0 field is detected in real time to avoid prediction errors caused by the inaccurate background B0 field. In the present invention, standard background B0 field maps may further be established for different body parts to calibrate background B0 field maps, so as to obtain highly accurate background B0 field maps in real time.

Sixth Embodiment

Figure 10:
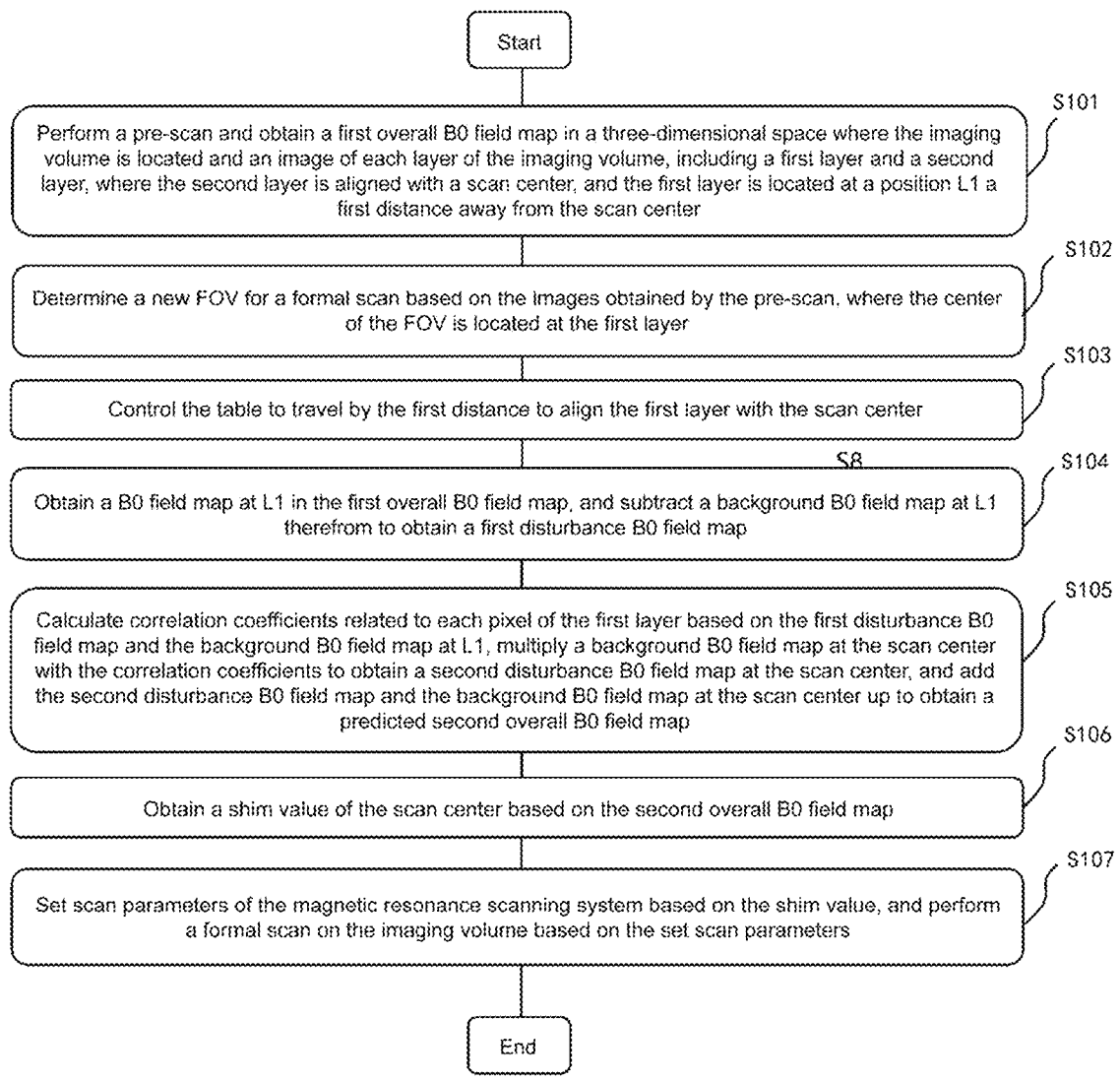
FIG. 10 is a flowchart of an example of a magnetic resonance scanning method according to a sixth embodiment of the present invention.
Figure 11:
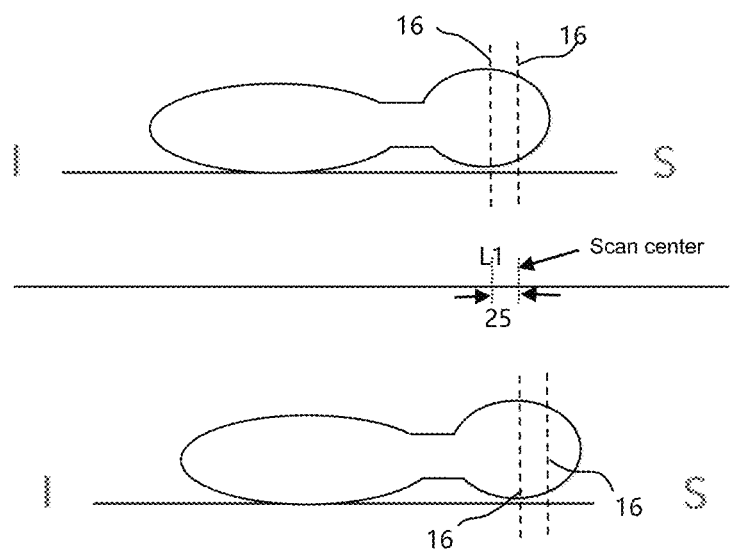
FIG. 11 schematically illustrates an object during an imaging scan and two layers in an imaging volume thereof.

FIG. 10 is a flowchart of an imaging scan method provided in the sixth embodiment of the present invention, where an example of using any of the aforementioned embodiments to predict an overall B0 field map and perform an imaging scan on an imaging volume based on the predicted overall B0 field map is shown. FIG. 11 schematically illustrates an object 16 during an imaging scan and two layers 161 and 162 of an imaging volume thereof, where the upper figure in FIG. 10 illustrates a positional relationship between the two layers and a scan center when a pre-scan is performed, and the lower figure in FIG. 10 illustrates a positional relationship between the two layers and the scan center when a formal scan is performed.

With reference to FIG. 10 and FIG. 11, in step S101: a pre-scan is performed to obtain a first overall B0 field map in a three-dimensional space where the imaging volume is located and an image of each layer of the imaging volume. At this time, the layer 162 is aligned with the scan center, and the layer 161 is located at a position L1 25 millimeters away from the scan center. In FIG. 11, I represents a side close to the feet of the object, S represents the side close to the head of the object, and the table can carry the object to travel toward the I side or the S side in a Z direction.

In step S102: a new FOV for a formal scan is determines based on the images obtained by the pre-scan, where the center of the FOV is located at the layer 161.

In step S103: the table is controlled to travel by 25 millimeters to align the layer 161 with the scan center. In this step, the layer 161 may also not be aligned with the scan center; then, in subsequent prediction, an overall B0 field map at other position is predicted. Thus, in the embodiment of the present invention, for some or all layers of the imaging volume, overall B0 field maps at positions where the layers are located in the next scan can be predicted.

In step S104: an overall B0 field map at L1 in the first overall B0 field map is obtained, and a background B0 field map at L1 is subtracted therefrom to obtain a first disturbance B0 field map.

In step S105: correlation coefficients related to each pixel of the layer 161 is calculated based on the first disturbance B0 field map and the background B0 field map at L1, a background B0 field map at the scan center is multiplied by the correlation coefficients to obtain a second disturbance B0 field map at the scan center, and the second disturbance B0 field map and the background B0 field map at the scan center are added up to obtain a predicted second overall B0 field map.

In step S106: a shim value of the scan center is obtained based on the second overall B0 field map. When second overall B0 field maps have been predicted for all positions in the three-dimensional space where the imaging volume is currently located, an overall B0 field map throughout the space is obtained.

In step S107: scan parameters of the magnetic resonance scanning system are set based on the shim value, and a formal scan is performed on the imaging volume based on the set scan parameters. The scan parameters may include a gradient shim value and a central frequency. The central frequency is a resonant frequency of protons of tissue of interest, and changes based on the change in the shimmed B0 field map, so as to better excite the tissue of interest. The gradient shim value may include an increment or decrement of a current applied to the gradient coil, where the current of the gradient coil is increased or decreased based on the shim value to obtain a desired uniform B0 field value.

When a technique of automatically shimming the B0 field is used to separately shim the predicted overall B0 field map and the actually scanned overall B0 field map, it is found that shim values of the two overall B0 field maps are close to each other. This indicates that the overall B0 field map predicted using the embodiment of the present invention and the actually scanned overall B0 field map are close.

Based on the above example, the magnetic resonance scanning method provided in the sixth embodiment of the present invention may include:

performing a current imaging scan (for example, the aforementioned formal scan) on the imaging volume based on the predicted overall B0 field map, which includes: obtaining a shim value at a current position based on the predicted overall B0 field map, and further adjusting, based on the shim value, scan parameters of the current imaging scan, for example, a parameter related to the gradient shim value and a parameter related to the central frequency. In this embodiment, the predicted overall B0 field map is obtained based on a disturbance B0 field map and a background B0 field map at a position of the imaging volume in a previous imaging scan (for example, the aforementioned pre-scan) and a background B0 field map at a position of the imaging volume in the current imaging scan. For example, an overall B0 field map at a position of the imaging volume in the current imaging scan may be predicted using any of the methods in the first to fifth embodiments.

Seventh Embodiment

Figure 12:
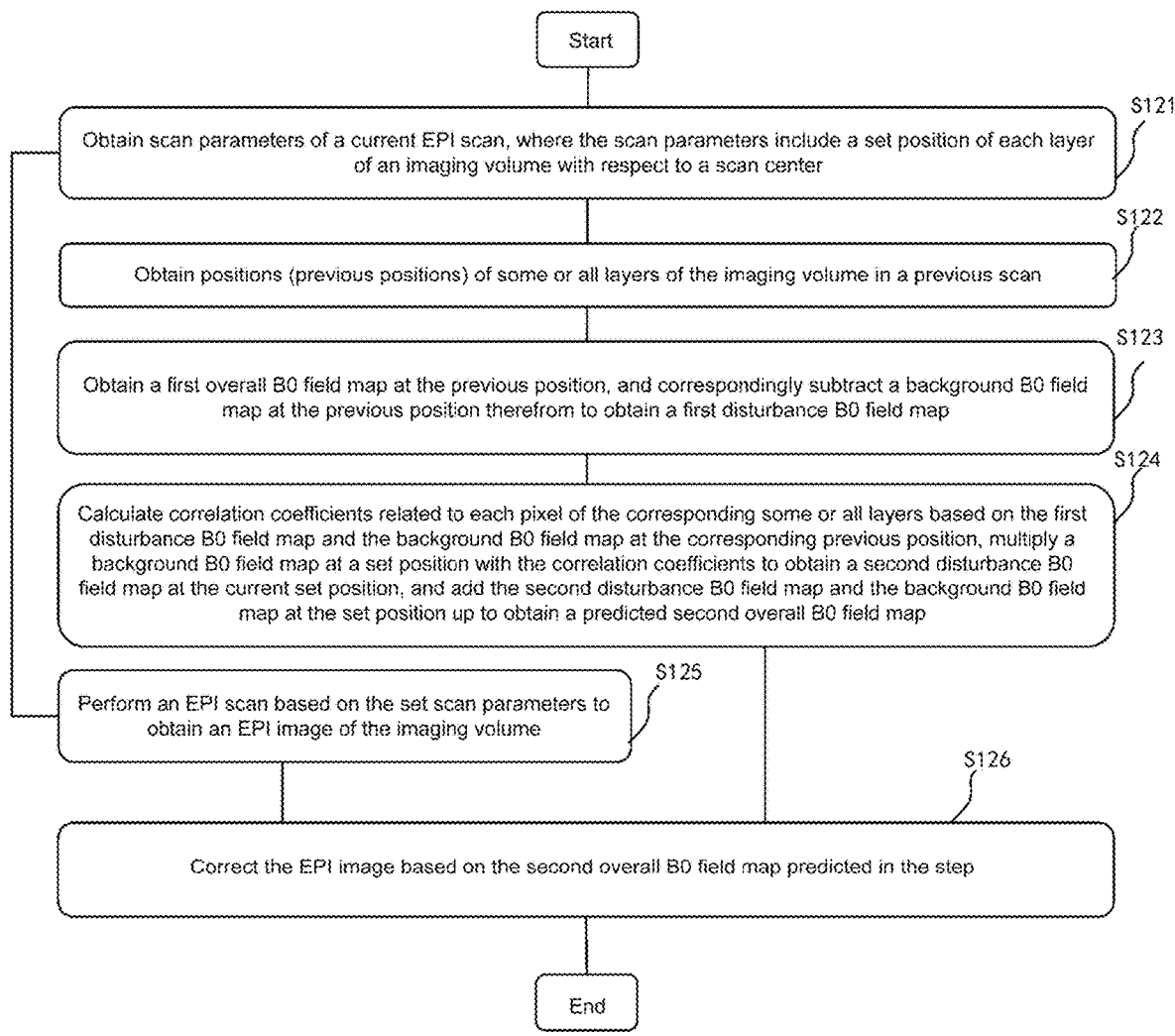
FIG. 12 is a flowchart of an example of a magnetic resonance scanning method according to a seventh embodiment of the present invention.

FIG. 12 is a flowchart of a magnetic resonance scanning method according to the seventh embodiment of the present invention, where an example of predicting an overall B0 field map in an EPI (echo planar imaging) scan and performing distortion correction on an EPI image based on the predicted overall B0 field map is shown.

As shown in FIG. 12, in step S121: scan parameters of a current EPI scan are obtained, where the scan parameters include a set position of each layer of an imaging volume with respect to a scan center.

In step S122: positions (previous positions) of some or all layers of the imaging volume in a previous scan are obtained, where the previous scan may be a pre-scan or other scan on other volume approaching the current imaging volume.

In step S123: a first overall B0 field map at the previous position is obtained, and a background B0 field map at the previous position is correspondingly subtracted therefrom to obtain a first disturbance B0 field map.

In step S124: correlation coefficients related to each pixel of the corresponding some or all layers are calculated based on the first disturbance B0 field map and the background B0 field map at the corresponding previous position, a background B0 field map at a set position is multiplied by the correlation coefficients to obtain a second disturbance B0 field map at the current set position, and the second disturbance B0 field map and the background B0 field map at the set position are added up to obtain a predicted second overall B0 field map.

In step S125: an EPI scan is performed based on the scan parameters set in step S111 to obtain an EPI image of the imaging volume.

In step S126: the EPI image is corrected based on the second overall B0 field map predicted in step S114, where the correction of an EPI image based on an overall B0 field (or a disturbance B0 field) is a known technique in the art and will not be described again. It should be noted that EPI is merely an application of an example, and similar methods may also be used for image correction in other applications sensitive to the disturbance B0 field. The aforementioned step S126 may be performed in the process of image post-processing.

Figures 13, 14, 15:
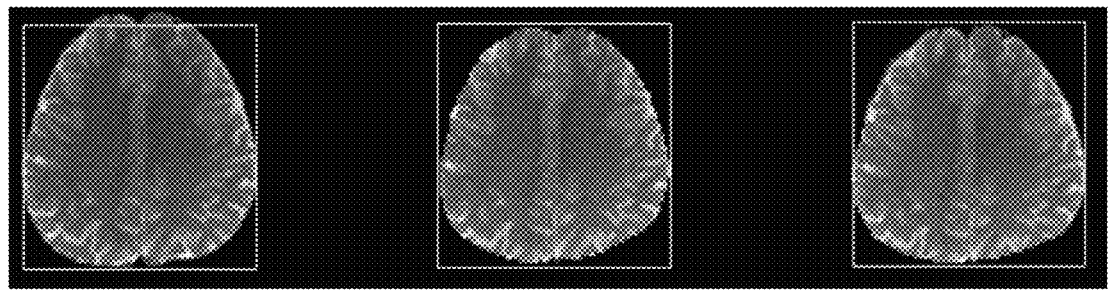
FIG. 13 illustrates an EPI image obtained in conventional EPI.
FIG. 14 illustrates an image obtained after the EPI image is calibrated based on an actually scanned B0 field map.
FIG. 15 illustrates an image obtained after the EPI image is calibrated based on an B0 field map predicted using the embodiment of the present invention.

FIG. 13 illustrates an EPI image obtained in conventional EPI. Geometric deformation (distortion) may exist in the conventional EPI since a B0 field map obtained by scanning is less accurate. For example, the contour of an imaged part changes and exceeds the border shown in the figure. FIG. 14 illustrates an image obtained after the EPI image shown in FIG. 10 is corrected based on an actually scanned B0 field map. FIG. 15 illustrates an image obtained after the EPI image shown in FIG. 10 is corrected based on an B0 field map predicted using the embodiment of the present invention. Upon comparison between FIG. 14 and FIG. 15, calibration of the EPI image based on the B0 field map predicted using the method in the embodiment of the present invention significantly alleviates the problem of distortion in the EPI image and achieves an effect substantially equivalent to that of correcting the EPI image using the actually measured B0 field map.

Thus, the magnetic resonance scanning method in the embodiment of the present invention may further include the following steps: when the preset layer is at the second position (or the imaging volume is at the current position), executing an imaging scan sequence on the imaging volume to obtain an image of the imaging volume; and correcting the image of the preset layer based on the predicted overall B0 field map at the second position.

Based on the above description, an embodiment of the present invention may further provide a magnetic resonance scanning system, which includes a scanner and a controller, where the scanner includes a table configured to carry an object to move, having a plurality of scan positions in a traveling direction of the table, for example, including at least the aforementioned first position and second position. The controller is configured to control the scanner to perform an imaging scan on an imaging volume of the object to obtain an image of the imaging volume, including performing any of the magnetic resonance scanning methods according to the first to seventh embodiments.

The structure and working principle of the magnetic resonance imaging system may be similar to those of the system shown in FIG. 1, and will not described herein again.

Based on the above description, an embodiment of the present invention may further provide a computer-readable storage medium in which computer-readable instructions are stored, where the computer-readable instructions are used to control a magnetic resonance scanning system to perform the magnetic resonance scanning method according to any one of the embodiments described above. The computer-readable storage medium may be similar to the storage medium in the controller 120 in the system shown in FIG. 1.

As used herein, an element or step described as singular and preceded by the word "a" or "an" should be understood as not excluding such element or step being plural, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements that do not have such property. The terms "including" and "in which" are used as the plain-language equivalents of the respective terms "comprising" and "wherein". Furthermore, in the appended claims, the terms "first", "second," "third" and so on are used merely as labels, and are not intended to impose numerical requirements or a particular positional order on their objects.

This written description uses examples to disclose the present invention, including the best mode, and also to enable those of ordinary skill in the relevant art to implement the present invention, including making and using any devices or systems and performing any incorporated methods. The patentable scope of the present invention is defined by the claims, and may include other examples that occur to those skilled in the art. Such other examples are intended to be within the scope of the claims if they have structural elements that do not differ from the literal language of the claims, or if they include equivalent structural elements without substantial differences from the literal language of the claims.

The invention claimed is:

1. A magnetic resonance scanning method, comprising:
when an imaging volume of an object is at a current position, performing a current imaging scan sequence including a first diagnostic scan on the imaging volume based on a predicted overall B0 field map at the current position;
wherein the predicted overall B0 field map is obtained based on a background B0 field map and an overall B0 field map at a previous position of the imaging volume obtained in a previous imaging scan sequence including a second diagnostic scan; and
wherein the background B0 field map comprises a background B0 field map at the previous position and a background B0 field map at the current position, and the predicted overall B0 field map is predicted based on the background B0 field map at the current position, a disturbance B0 field map at the previous position, and the background B0 field map at the previous position, wherein the disturbance B0 field map at the previous position is obtained by subtracting the background B0 field map at the previous position from the overall B0 field map at the previous position; and
wherein the previous position comprises a first position of a preset layer of the imaging volume, the current position comprises a second position of the preset layer, the predicted overall B0 field map comprises an overall B0 field map at the second position, and the method further comprises the following steps to obtain the predicted overall B0 field map:
obtaining an overall B0 field map at the first position and a disturbance B0 field map at the first position when the preset layer of the imaging volume is at the first position, wherein the disturbance B0 field map at the first position is a difference between the overall B0 field map at the first position and a background B0 field map at the first position; and
predicting the overall B0 field map at the second position when the preset layer is at the second position, wherein the prediction is performed based on the disturbance B0 field map at the first position, the background B0 field map at the first position, and a background B0 field map at the second position; and
wherein the predicting comprises:
obtaining correlation coefficients related to the preset layer, wherein the correlation coefficients are obtained based on the disturbance B0 field map at the first position and the background B0 field map at the first position;
correlating the correlation coefficients with the background B0 field map at the second position to obtain a disturbance B0 field map at the second position; and
calculating the overall B0 field map at the second position based on the disturbance B0 field map at the second position and the background B0 field map at the second position.

2. The scanning method according to claim 1, wherein the performing the current imaging scan sequence comprises: obtaining a shim value of the current imaging scan sequence based on the predicted overall B0 field map at the current position.

3. The scanning method according to claim 2, wherein the performing the current imaging scan sequence comprises: adjusting scan parameters of the current imaging scan sequence based on the shim value of the current imaging scan sequence.

4. The scanning method according to claim 1, wherein the overall B0 field map at the previous position is obtained based on a B0 field scan performed on the imaging volume in the previous imaging scan sequence.

5. The method according to claim 1, wherein the predicting comprises: adding the disturbance B0 field map at the second position to the background B0 field map at the second position to obtain the overall B0 field map at the second position.

6. The method according to claim 5, wherein the correlation coefficients comprise coefficients related to a linear relationship between the disturbance B0 field map at the first position and the background B0 field map at the first position.

7. The method according to claim 6, wherein the correlation coefficients comprise a slope value in the linear relationship.

8. The method according to claim 6, wherein the method further comprises the following steps to obtain the predicted overall B0 field map:
obtaining an overall B0 field map and a disturbance B0 field map at a third position of the preset layer of the imaging volume when the preset layer is at the third position, wherein the disturbance B0 field map at the third position is a difference between the overall B0 field map at the third position and a background B0 field map at the third position; and
predicting, based on the disturbance B0 field map at the first position, the background B0 field map at the first position, the disturbance B0 field map at the third position, the background B0 field map at the third position, and the background B0 field map at the second position, the overall B0 field map at the second position when the preset layer is at the second position.

9. The method according to claim 8, wherein the correlation coefficients are obtained based on the disturbance B0 field map at the first position, the background B0 field map at the first position, the disturbance B0 field map at the third position, and the background B0 field map at the third position, and the correlation coefficients further comprise a slope value and an intercept value in the linear relationship.

10. The method according to claim 1, wherein the obtaining the correlation coefficients comprises: obtaining a plurality of correlation coefficients related to a plurality of pixels of the preset layer based on a plurality of disturbance B0 field strengths of the disturbance B0 field map at the first position and a plurality of corresponding background B0 field strengths in the background B0 field map at the first position, and the predicting comprises: calculating a plurality of disturbance B0 field strengths at the second position based on the plurality of correlation coefficients and a plurality of corresponding background B0 field strengths in the background B0 field map at the second position, and calculating a plurality of overall B0 field strengths at the second position based on the plurality of background B0 field strengths at the second position and the plurality of disturbance B0 field strengths at the second position.

11. The method according to claim 1, further comprising:
performing low-pass filtering on the overall B0 field map at the previous position to obtain a reference background B0 field map; and determining whether a difference between the reference background B0 field map and the background B0 field map is less than a first preset value, and if not, issuing alarm information.

12. The method according to claim 1, further comprising:
obtaining a standard background B0 field map related to a body part where the imaging volume is located;
calibrating the background B0 field map based on the standard background B0 field map to obtain a calibrated background B0 field map;
performing low-pass filtering on the overall B0 field map at the previous position to obtain a reference background B0 field map; and
determining whether a difference between the reference background B0 field map and the calibrated background B0 field map is less than a second preset value, and if so, using the calibrated background B0 field map as the background B0 field map to predict the overall B0 field map at the current position.

13. The method according to claim 12, further comprising:
obtaining, based on a plurality of reference background B0 field maps related to the body part where the imaging volume is located, a standard background B0 field map related to the body part where the imaging volume is located.

14. The method according to claim 13, wherein the plurality of reference background B0 field maps related to the body part where the imaging volume is located are respectively obtained during a plurality of scans performed on the body part where the imaging volume is located.

15. The method according to claim 13, wherein data fusion is performed on the plurality of reference background B0 field maps related to the body part where the imaging volume is located to obtain the standard background B0 field map.

16. The method according to claim 13, further comprising: updating, based on the reference background B0 field map obtained by performing low-pass filtering on the overall B0 field map at the previous position, the standard background B0 field map related to the body part where the imaging volume is located.

17. The method according to claim 14, wherein the reference background B0 field map obtained by performing low-pass filtering on the overall B0 field map at the previous position, the background B0 field map, the standard B0 field map, and the calibrated background B0 field map are all represented in a form of multi-order harmonic decomposition.

18. The method according to claim 17, wherein the performing the current imaging scan sequence on the imaging volume of the object further comprises:
executing an imaging scan sequence on the imaging volume to obtain an image of the imaging volume; and
correcting the image of the imaging volume based on the predicted overall B0 field map.

19. A magnetic resonance scanning system, comprising:
a scanner, comprising a table configured to carry an object to move, having a plurality of scan positions in a traveling direction of the table; and
a controller, configured to control the scanner to perform an imaging scan sequence on an imaging volume of the object to obtain an image of the imaging volume, comprising performing the magnetic resonance scanning method according to claim 1.

20. A non-transitory computer-readable storage medium, for storing computer-readable instructions, wherein the computer-readable instructions are used for performing the method according to claim 1.

* * * * *